(12) United States Patent
Engelbrecht

(10) Patent No.: US 7,264,882 B2
(45) Date of Patent: Sep. 4, 2007

(54) ADHESIVE FLUORIDE VARNISH

(75) Inventor: Juergen Engelbrecht, Hamburg (DE)

(73) Assignee: S & C Polymer Silicon- und Composite-Spezialitaten GmbH, Elmshorn (DE)

( * ) Notice: Subject to any disclaimer, the term of this patent is extended or adjusted under 35 U.S.C. 154(b) by 0 days.

(21) Appl. No.: 10/343,521

(22) PCT Filed: Aug. 6, 2001

(86) PCT No.: PCT/EP01/09072

§ 371 (c)(1),
(2), (4) Date: May 30, 2003

(87) PCT Pub. No.: WO02/11681

PCT Pub. Date: Feb. 14, 2002

(65) Prior Publication Data

US 2003/0183124 A1    Oct. 2, 2003

(30) Foreign Application Priority Data

Aug. 7, 2000 (DE) .................... 100 39 298
Aug. 17, 2000 (DE) .................... 100 40 716

(51) Int. Cl.
*B32B 25/20*    (2006.01)
(52) U.S. Cl. .............. 428/447; 524/588; 524/434; 524/424; 524/127; 528/31; 528/15; 433/217.1
(58) Field of Classification Search ........... 524/588, 524/434, 424, 127; 528/31, 15; 433/217.1; 428/447

See application file for complete search history.

(56) References Cited

U.S. PATENT DOCUMENTS

| | | | | |
|---|---|---|---|---|
| 3,124,512 A | * | 3/1964 | Schmidt et al. ............... 424/52 |
| 4,921,988 A | * | 5/1990 | Takatsuna et al. ........... 556/413 |
| 5,139,768 A | * | 8/1992 | Friedman ..................... 424/45 |
| 5,260,402 A | * | 11/1993 | Weitemeyer et al. ......... 528/29 |
| 5,385,960 A | * | 1/1995 | Emmons et al. ............ 523/205 |
| 5,494,618 A | * | 2/1996 | Sitzmann et al. ........... 264/401 |
| 6,120,294 A | * | 9/2000 | Engelbrecht et al. .... 433/228.1 |
| 6,335,413 B1 | * | 1/2002 | Zech et al. ................... 528/32 |
| 6,353,041 B1 | * | 3/2002 | Qian .......................... 523/116 |
| 6,566,479 B1 | * | 5/2003 | Bublewitz et al. ............ 528/15 |
| 6,610,276 B2 | * | 8/2003 | Melman ...................... 424/57 |

FOREIGN PATENT DOCUMENTS

| | | | |
|---|---|---|---|
| DE | 199 34 117 A | | 8/2000 |
| EP | 1 022 012 A | | 7/2000 |
| JP | 06-024927 | * | 2/1994 |
| JP | 11-209213 A | | 8/1999 |
| WO | WO92/16183 A | | 10/1992 |
| WO | 99/09934 | * | 3/1999 |
| WO | 99/37272 | * | 7/1999 |

* cited by examiner

*Primary Examiner*—Kuo-Liang Peng
(74) *Attorney, Agent, or Firm*—Frommer Lawrence & Haug LLP; Ronald R. Santucci

(57) ABSTRACT

The invention relates to mixtures comprising polymers containing hydrogen-siloxane groups and fluoride, in addition to the use of said mixtures as a dental scaling varnish and fluoridation varnish and as a desensitising agent, in addition to the use of said mixtures as a protective covering for glasionomer cement fillings.

16 Claims, No Drawings

ADHESIVE FLUORIDE VARNISH

This application is a 371 of PCT/EP01/09072 filed on Aug. 6, 2001, published on Feb. 14, 2002 under publication number WO 02/1 1681 A1 which claims priority benefits from German patent application number DE 100 39 298.9 filed Aug. 7, 2000 and German patent application number DE 10040716.1 filed Aug. 17, 2000.

This invention relates to mixtures containing polymers having hydrogen-siloxane groups and fluorides as well as their use as a dental sealing varnish and fluoridation varnish, a desensitizing agent and a protective varnish for glass ionomer cement fillings.

Protective varnishes for teeth have been in use successfully for almost three decades. First, there are the fissure-sealing varnishes based on photopolymerizable (single component) or self-polymerizing (dual-component) methacrylate resins. Their use requires prior superficial etching of the enamel surface with phosphoric acid. Adhesion to dentin is micromechanical and the protective coating seals the microfissures for a period of years. In some formulations, the varnish contains such additives as fluoride salts, a glass powder that releases fluoride or organic fluoride compounds. Traditional examples include Delton (Dentsply, USA), Visio-Seal (Espe, Germany).

Secondly, there are fluoride varnishes for teeth, polymer solutions containing fluorides which leave behind a colorless protective film resembling nail polish on the surface of the tooth after evaporation of the solvent. Films of this type remain on the surface of the tooth for only a short period of time and are used only as a depot for the fluoride to be administered. Examples of this group of fluoride varnishes include products such as Bifluorid (Voco, Germany) and Duraphat (Colgate, Germany).

Adducts of silicones and acid-containing monomers constitute another development in the field of dental varnishes (K. G. Bohlig et al., abstract 1036, J. Dent. Research, vol. 79, Spec. Issue 2000). In this case, polymers containing fragments of silicone with SiOH and —COOH groups are applied in the form of a solution to the dental surface. Their dual functionality makes it possible for them to adhere to the enamel surface without superficial etching (—COOH) as well as to undergo self-crosslinking in the presence of potential condensation catalysts and crosslinking agents (SiOSiOH+Si(OR)$_4$+HOSiOSi ---->SiOSiO—OSiO—SiOSi). Varnishes of this type are more hydrophobic than those in the past and therefore are less easily washed out, adhere well and are quite durable when crosslinked.

PCT/EP 0001042 and European Patent 0 632 060 A1 describe adhesives of copolymers containing hydrogen-siloxane groups and solutions thereof. Adhesives according to PCT/EP 0001042 unexpectedly also adhere to tooth enamel.

The object of the present invention was to discover a neutral varnish which would be capable of forming an adhering, potentially crosslinking dental coating and could serve as a carrier for fluoridation agents.

According to this invention, this object has been achieved through mixtures containing
  a) polymers having hydrogen-siloxane groups,
  b) fluorides,
  c) optionally a platinum catalyst, and
  d) optionally vinyl compounds.

The mixtures according to this invention contain polymers having hydrogen-siloxane groups as an important substance which forms a varnish that adheres to dental substance. The basic structure of these polymers may be, for example, copolymers of methyl methacrylate and allyl methacrylate with hydrogen-siloxane grafted onto them. They may also be copolymers such as those described in detail in European Patent 0 632 060 A1 or, especially preferably, copolymers obtained by direct polymerization of hydrogen-siloxanes, as described in the attached PCT/EP 0001042 and in Unexamined Japanese Patent Specification (A) No. HEI 10-25322 published on Jan. 27, 1998. With respect to the (co)polymers and their production, explicit reference is made to the three publications cited above. The SiH groups of the hydrogen-siloxane units are evidently capable of reacting with the POH groups of apatite dental substance so that bonding of the varnish to dental substance comes about by a chemical route without prior mechanical roughening (etching).

The fluorides that are used may be the same as those contained in conventional commercial fluoride varnishes. Fluorides used in many cases are organic or inorganic fluorides such as sodium fluoride, potassium fluoride, calcium fluoride, strontium fluoride, zinc fluoride, tin fluoride, sodium or potassium hexafluorophosphate, sodium or potassium hexafluoroaluminate, ammonium fluoride or organic fluorides such as amine fluorides, e.g., cetylamine hydrofluoride, bis(hydroxyethyl)aminopropyl-N-hydroxyethyloctadecylamine dihydrofluoride.

According to this invention, solid fluorides may be ground to the finest possible particle size, e.g., to an average particle size between 1 and 10 microns or dissolved in one of the solvents mentioned below.

Liquid fluorides may be used as such or dissolved in one of the solvents listed below.

The mixtures according to this invention preferably contain the polymers having hydrogen-siloxane groups and fluorides in a weight ratio of 100:1 to 10:5, especially preferably in a weight ratio of 20:1 to 10:4.

In addition, they may contain up to 10 parts by weight, preferably up to 1 part by weight of a vinyl compound, up to 500 ppm, preferably up to 50 ppm platinum catalyst and up to 80 parts by weight, preferably up to 20 parts by weight polymer(s) without hydrogen-siloxane groups.

The SiH groups of the hydrogen-siloxane units of the polymers used according to this invention have a tendency to undergo hydrolysis in a humid or moist medium (SiH ---->SiOH), and they tend to crosslink and split off hydrogen (SiH+SiOH ---->SiOSi+H$_2$). In the oral medium, this cleavage of hydrogen takes place after application of the dental varnish, thus leading to a subsequent crosslinking. Thus, a catalyst is not absolutely necessary.

If it is desirable to achieve rapid crosslinking of the varnish polymers, especially in the presence of vinyl compounds or other compounds containing double bonds, then it may be beneficial to add a catalyst, if necessary, capable of catalyzing the SiH+SiOH reaction or the SiH+—CR=CR$_2$ reaction. These catalysts are known to be compounds of platinum or palladium as well as alloys thereof. Platinum(0) compounds produced by starting with platinum hexachloroplatinate are especially suitable; these compounds are conventionally used in addition-crosslinking vinyl-polysiloxane/hydrogen-polysiloxane systems.

Examples of such catalysts include: PT$_x$ (divinyltetramethyldisiloxane)$_y$ of platinum(0).

optionally added vinyl compounds should preferably be divinyl compounds. However, compounds with more than two vinyl groups may also be appropriate, e.g., when a higher degree of crosslinking is to be achieved. Preferred divinyl compounds include divinyl ethers such as the divinyl ether of triethylene glycol or cyclohexanediol or divinylpolysiloxanes such as those used in addition-crosslinking silicones or divinyltetramethyldisiloxane.

Mixtures according to this invention may additionally also contain polymers which do not have any SiH groups. Examples of these include polymethacrylates, polycarbonates, polyesters and similar polymers, if they are soluble in the mixture and are compatible with the system.

Likewise, mixtures according to this invention may contain solvents, preferably readily volatile solvents which make it possible to apply the varnish as a very thin film. Suitable solvents include especially readily volatile inert solvents such as halogenated or non-halogenated aliphatic or aromatic hydrocarbons, ethers, ketones, esters or cyclic siloxanes. In particular, physiologically safe solvents may also be used and especially preferably solvents in which the soluble fluorides used according to this invention are readily soluble.

For stabilization of insoluble fluoride powder particles, additives may be added to the mixtures according to this invention to counteract premature separation. Such substances may include for example pyrogenic silicas or modified cellulose. Additives in the form of agents to prevent caking of deposited particles may also be appropriate and indicated when the mixtures are to be stored for a long period of time and should be rehomogenizable by shaking gently. Compounds or agents having biostatic, biocidal or pharmaceutical effects such as antibacterial or anti-inflammatory effects may also be added. Biocidal compounds or agents are those which kill bacteria, viruses and/or fungi, while biostatic compounds or agents inhibit the growth of bacteria, viruses and/or fungi.

According to another embodiment, the mixtures according to this invention may also contain hydrogen-siloxanes different from those according to a). Such hydrogen-siloxanes are preferably polysiloxanes having at least two SiH groups, preferably three SiH groups.

Due to the presence of phosphoric acid, mixtures according to this invention are excellently suited for use as adhesive dental varnishes for sealing fissures without requiring etching by phosphoric acid. Due to the lack of etching, it is possible to prevent damage to healthy dental enamel beyond the sealing area, while on the other hand there are no unetched non-bonding surfaces beneath the sealing. Another major advantage is the fact that sealing with varnishes according to this invention can be supplemented easily, but this is not possible on such an intimate basis with fissure sealing materials based on methacrylate. Another advantage is that sealing according to this invention can be performed in an extremely thin layer, which is not possible with methacrylate sealing because of the 50-100 micron-thick inhibition layer due to the presence of atmospheric oxygen.

Also as an adhesive varnish for fluoridation of dentin, the varnishes according to this invention are superior to the fluoridation varnishes used in the past. They adhere chemically, i.e., much better, are more hydrophobic, are stable for several months even on load-bearing surfaces and can easily be supplemented at any time.

Mixtures according to this invention are also suitable for desensitization of the neck of the tooth. When applied, they rapidly seal open channels in the dental enamel after the solvent has evaporated and thus prevent the painful symptoms.

It has unexpectedly also been found that varnishes according to this invention are also excellently suited as protective varnishes for cements such as dental cement. For example, the surface of freshly prepared glass ionomer cement applied as a filling must be provided with a protective varnish. In the past, protective varnishes of this type have been solutions of polymers such as polymethyl methacrylates, polyesters, polycarbonates or the like. These varnishes remain on the surface of the fresh cement filling for only a few hours or days; they adhere only mechanically and are washed away quickly. Although they do largely fulfill their function because the glass ionomer cements must mainly be protected in the first minutes to hours, namely until the hardening mechanism has led to structures which are less soluble and have three-dimensional crosslinking, nevertheless the varnishes according to this invention have the advantage that, first of all, they are more hydrophobic and thus they are better in preventing the underlying layers of cement from dissolving away; secondly, the fluoride content of the varnishes according to this invention protects and supplements the fluoride reservoir of the glass ionomer cement and thus prolongs its efficacy. Subsequent application of varnishes according to this invention to glass ionomer fillings may also lead to a "recharging" of fluoride in the glass ionomer filling, which is known to be possible with fluoride applications and which can take place intensely and permanently due to the prolonged presence of the varnish according to this invention on the glass ionomer surface.

All the quantity amounts given below are based on weight, unless otherwise indicated.

EXAMPLES

Example 1

Fissure Sealing Material

A copolymer containing hydrogen-siloxane was produced according to example 1 of PCT/EP 00/01042. A mixture according to this invention was prepared fresh from 10 parts of the polymer, 2 parts extremely finely ground sodium fluoride, 0.2 parts ethylcellulose, 0.05 parts titanium dioxide and 57 parts ethyl acetate. After brief but intense mechanical cleaning with a rotating brush with polish paste, cleaning with ethanol and subsequent rinsing with water, drying with oil-free air, the fissures of the occlusive surface of a deciduous molar tooth was coated twice with a thin layer of the solution using a dental brush. After eight weeks, the sealing was still visible.

Example 2

Antiplaque Fluoride Varnish

A mixture according to this invention was prepared fresh from 10 parts of the polymer from example 1, 0.2 parts extremely finely ground zinc fluoride, 0.1 parts Aerosil 810 (Degussa), 89 parts ethyl acetate. After a brief but intense mechanical cleaning with a rotating brush using polish paste, cleaning with ethanol and subsequent rinsing with water, drying with oil-free air, the labial surface of a front tooth was coated once with a thin layer of the solution using a dental brush. After 8 weeks, the tooth was checked for plaque with the help of a plaque staining test. No plaque could be detected on the surface treated according to this invention whereas all the other teeth had more or less pronounced plaque phenomena.

Example 3

Desensitizer

The solution from example 2 was placed on the neck of a sensitive tooth after appropriate pre-cleaning. After a brief period of time, the sensitivity had disappeared. After eight weeks, the thin layer of fluoride varnish was still discernible.

Example 4

Cement Varnish

A copolymer containing hydrogen-siloxane was prepared according to example 1 of PCT/EP 00/01042. A mixture according to this invention was prepared fresh from 12 parts of the polymer (see example 1), 1 part extremely finely ground sodium fluoride, 0.1 part ethylcellulose and 90 parts methyl ethyl ketone. A test body was produced from freshly prepared glass ionomer cement (Aqua Ionofil Plus, Voco, Germany), the surface was coated with the varnish according to this invention and the sample was placed immediately in water. The same procedure was repeated, but this time without treating the surface according to this invention. After one week, the samples were removed from the water. The surface of the test body treated according to this invention was much smoother and more scratch-resistant than the untreated test body.

The invention claimed is:

1. A method of adhering a varnish to teeth or cement fillings, comprising adhering to the teeth or cement filings a mixture containing:
   a. polymers with hydrogen-siloxane groups;
   b. fluorides,
   c. optionally a platinum catalyst,
   d. optionally vinyl compounds,
   wherein (a) are copolymers of unsaturated compounds onto which siloxanes containing SiH groups have been grafted; and
   wherein the mixture is a varnish comprising a sealing varnish for teeth, a fluoridation varnish, a neck desensitizer, a protective varnish for cement, and/or a protective varnish for dental cement.

2. The method according to claim 1, wherein the fluorides are inorganic fluorides such as sodium fluoride, potassium fluoride, calcium fluoride, strontium fluoride, zinc fluoride, tin fluoride, hexafluorophosphates, or amine fluorides.

3. The method according to claim 1, wherein the platinum catalyst is a compound of platinum (0).

4. The method according to claim 1, wherein the vinyl compounds have vinylsiloxane groups or vinyl ether groups.

5. The method according to claim 1, wherein the mixture also contains polymers without hydrogen-siloxane groups.

6. The method according to claim 1, wherein the mixture also contains readily volatile solvents.

7. The method according to claim 1, wherein the mixture also contains compounds or agents having a biostatic, biocidal or other pharmaceutical effect.

8. The method according to claim 1, wherein the mixture also contains hydrogen-siloxanes other than those according to (a).

9. A method of adhering a varnish to teeth or cement fillings, comprising adhering to the teeth or cement fillings a mixture containing:
   a. polymers with hydrogen-siloxane groups;
   b. fluorides;
   c. optionally a platinum catalyst;
   d optionally vinyl compounds;
   wherein (a) are copolymers of SiH groups-containing siloxanes with unsaturated compounds, and
   wherein the mixture is a varnish comprising a sealing varnish for teeth, a fluoridation varnish, a neck desensitizer, a protective varnish for cement, and/or a protective varnish for dental cement.

10. The method according to claim 9, wherein the fluorides are inorganic fluorides such as sodium fluoride, potassium fluoride, calcium fluoride, strontium fluoride, zinc fluoride, tin fluoride, hexafluorophosphates, or amine fluorides.

11. The method according to claim 9, wherein the platinum catalyst is a compound of platinum (0).

12. The method according to claim 9, wherein the vinyl compounds have vinylsiloxane groups or vinyl ether groups.

13. The method according to claim 9, wherein the mixture also contains polymers without hydrogen-siloxane groups.

14. The method according to claim 9, wherein the mixture also contains readily volatile solvents.

15. The method according to claim 9, wherein the mixture also contains compounds or agents having a biostatic, biocidal or other pharmaceutical effect.

16. The method according to claim 9, wherein the mixture also contains hydrogen siloxanes other than those according to (a).

* * * * *